(12) United States Patent
Deschaume et al.

(10) Patent No.: US 8,007,759 B2
(45) Date of Patent: Aug. 30, 2011

(54) PROCESS FOR PREPARING ALUMINIUM SPECIES

(75) Inventors: Olivier Deschaume, Montceau-les-Mines (FR); Carole Celia Perry, Nottingham (GB); Kirill Shafran, Wirral (GB)

(73) Assignee: Conopco Inc., Englewood Cliffs, NJ (US)

( * ) Notice: Subject to any disclaimer, the term of this patent is extended or adjusted under 35 U.S.C. 154(b) by 51 days.

(21) Appl. No.: 11/887,643

(22) PCT Filed: Mar. 22, 2006

(86) PCT No.: PCT/EP2006/002958
§ 371 (c)(1),
(2), (4) Date: Sep. 28, 2007

(87) PCT Pub. No.: WO2006/103092
PCT Pub. Date: Oct. 5, 2006

(65) Prior Publication Data
US 2009/0081117 A1    Mar. 26, 2009

(30) Foreign Application Priority Data

Mar. 31, 2005   (EP) .................................. 05252011

(51) Int. Cl.
*C01F 7/02* (2006.01)
*C01F 7/48* (2006.01)

(52) U.S. Cl. ........ 423/625; 423/112; 423/462; 423/495; 423/629; 252/181

(58) Field of Classification Search .................. 423/462, 423/467, 112, 495, DIG. 14, 629; 252/181
See application file for complete search history.

(56) References Cited

U.S. PATENT DOCUMENTS

| | | | | |
|---|---|---|---|---|
| 4,176,090 | A | 11/1979 | Vaughan et al. | 252/455 R |
| 4,271,043 | A | 6/1981 | Vaughan et al. | 252/455 R |
| 6,036,935 | A | 3/2000 | Dulko | 423/462 |
| 6,153,227 | A * | 11/2000 | Shibuya et al. | 424/539 |
| 6,911,481 | B2 * | 6/2005 | Tanaka et al. | 521/26 |
| 7,431,862 | B2 * | 10/2008 | Mehrotra et al. | 252/62.54 |

FOREIGN PATENT DOCUMENTS

| | | |
|---|---|---|
| EP | 0 183 171 | 3/1990 |
| EP | 0 451 395 | 8/1994 |
| GB | 1 568 831 | 6/1980 |

OTHER PUBLICATIONS

Fu et al. Aging Processes of Alumina Sol-Gels: Characterization of New Aluminum Polyoxycations by 27Al NMR Spectroscopy, Chem. Mater., 1991, 3, 602-610.*
Rowsell et al. "Speciation and Thermal Transformation in Alumina Sols: Structures of the Polyhydroxyoxoaluminum Cluster [Al30O8(OH)56(H2O)26]18+ and Its ä-Keggin Moiete", JACS, 2000, 122, 3777-3778.*
Hubicki et al. "Studies of the Sorption of Palladium(II) Ions from Model Chlorides Systems onto an Ion Exchanger Containing Isothiourea Groups and onto Weakly Basic Anion Exchangers of Various Types", Adsorption Science & Technology (2004), 22(8), 603-614.*
PCT International Search Report in PCT application PCT/EP2006/002958.
K. Shafran et al., "*High-Temperature Speciation Studies of Al-Ion Hydrolysis*", Advanced Engineering Materials, vol. 6, No. 10, 2004, pp. 836-839.
Kudryavtseva et al., "*Effect of microstructure on the stability of nanocrystalline tin dioxide ceramics*", Journal of Material Chem., 1997, vol. 7(11). pp. 2269-2272.
Tretyakov et al., "*Recent progress in cryochemical synthesis of oxide materials*", Journal of Material Chem., 1999, vol. 9, pp. 19-24.
Vertegel et al., "*The fractal particles of iron (III) hydroxonitrate: from solution to solid state*", Journal of Non-Crystalline Solids, vol. 181 (1995), pp. 146-150.
Berg, "*Die Lösungsgeschwindigkeit von Aluminum in Salpetersäure*", Z.anorg.allg. Chemie, vol. 269, 1952, pp. 213-217 (with English translation).
Vertegel et al., "*Visible spectra of fractal particles in colloidal solutions* ", Chemical Physics Letters, vol. 262 (1996), pp. 455-459.

* cited by examiner

*Primary Examiner* — Emily M Le
*Assistant Examiner* — Rebecca Lee
(74) *Attorney, Agent, or Firm* — Karen E. Klumas

(57) ABSTRACT

A static ion-exchange process for the preparation of a polynuclear Al species comprising the treatment of an aqueous aluminum chloride solution with a hydroxide-form ion-exchange resin at a temperature of from 5° C. to 60° C. for a period of at least 30 minutes.

14 Claims, No Drawings

PROCESS FOR PREPARING ALUMINIUM SPECIES

This invention is in the field of materials science and concerns a process for the controlled preparation of hydrolyzed aluminum species, in particular polynuclear Al species, specific examples being the species known as the $Al_{13}$-mer ($[Al_{13}O_4(OH)_{24}(H_2O)_{12}]^{7+}$) and the $Al_{30}$-mer ($[Al_{30}O_8(OH)_{56}(H_2O)_{26}]^{18+}$).

Polynuclear aluminum species are used in a number of materials science applications including the preparation of pillared clays, $Al_2O_3$ nanoparticles, antiperspirant actives, catalysts, and composite materials (see Shafran et al, *Adv. Eng. Materials*, 6(10), 2004, 836, for references to these applications).

The use of polynuclear aluminum species in antiperspirant (AP) actives has been particularly prevalent. Many AP actives include basic aluminum chloride species. These have the general formula $Al_2(OH)_{6-x}Cl_x$, where x is between about 0.5 and 5. Aluminium chlorohydrate (ACH) is a particular basic aluminum chloride in which x is 5. ACH has been widely used in the AP industry because of its relatively low acidity and subsequent low tendency to cause skin irritation.

The aqueous solution chemistry of basic aluminum chlorides in general, and ACH is particular, is rather complex (see "Antiperspirants and Deodorants", ed. Karl Laden, 1999, Chapter 4: "Chemistry of ACH and Activated ACH", by Fitzgerald and Rosenberg). The preparation of the materials involves multiple hydrolysis and condensation reactions, typically resulting in a plethora of species being produced. Whilst the reactions can be difficult to control, it has been identified that some polynuclear Al species are produced and that these are desirable for higher AP efficacy (vide infra). Fitzgerald and Rosenberg describe the $Al_{13}$-mer polynuclear species in some detail; however, other desirable polynuclear Al species have been identified more recently, such as the $Al_{30}$-mer (Roswell and Nazar, *J. Am. Chem. Soc.*, 122, 2000, 3777; L. Allouche et al, *Angew. Chem. Int. Edit.*, 2000, 39, 511).

Methods have been developed to prepare ACH actives that are rich in polynuclear Al species, such actives sometimes being called "activated" ACH. GB 1,568,831 (Unilever, 1976) describes a route involving heating a solution of ACH under controlled conditions to give polymeric species having a size above 100 Angstroms. EP 183,171 B1 (Armour Pharm. Co., 1985) describes a route involving specific heating, drying, and cooling steps, resulting in an ACH having enhanced activity. EP 451,395 B1 (Unilever, 1990) describes a process involving the production of ACH having a Band III fraction of at least 20%, the Band III material having particularly good AP efficacy.

In general, the prior art routes to ACH of enhanced activity are somewhat complex and/or involve heating regimes that last for many hours and/or require high temperatures, for example in excess of 100° C. Clearly, heating to high temperature or for prolonged lengths of time requires much energy, and processes involving such procedures are undesirable because of the cost involved. In addition, whilst the heating can lead to the production of the desired polynuclear ACH component(s), it can also reduce the selectivity of the reaction.

The majority of prior art routes to activated ACH have been based on the electrochemical reaction of aluminum metal with either HCl or $AlCl_3$ solution. This route is attractive due to the relatively low cost of starting materials and the low number of reaction stages (usually two: the dissolution of the Al metal and the thermal ageing of the resulting solution). Unfortunately, there are several problems associated with this type of ACH synthesis:

(1) Dissolution of the Al metal is a difficult and slow process due to the Al metal being 'passivated' by an aluminum oxide film formed on its surface. Whilst mercury may be used to partially alleviate this problem, the use of mercury is undesirable because of its toxicity.
(2) During the initial stages of Al metal dissolution, hydrogen gas is produced; this is potentially explosive and can raise safety concerns.
(3) Since dissolution of the Al metal is slow, the reaction stoichiometry varies throughout the course of the dissolution/reaction and this can result in a multitude of species being produced.

None of the above routes to enhanced activity ACH take advantage of the procedure of the invention, which involves relatively low temperatures and the use of an static ion-exchange process. Whilst such procedures have not previously been used in the manufacture of polynuclear Al species, they have been used in other fields. For example, the preparation of iron oxide using a hydroxide-form ion-exchange resin is described by Vertegel et al (*J. Non-Cryst. Solids*, 181, 1995, 146). It has also been reported that such techniques have been used to prepare $Al_2O_3$, $Cr_2O_3$ and $Fe_2O_3$ (Kudryavtseva et al, *J. Mater. Chem.*, 7(11), 1997, 2269).

Dynamic ion-exchange, whereby an aqueous solution of $AlX_3$ is passed through an ion-exchange column in $OH^-$ form, is referred to in U.S. Pat. No. 4,176,090 (Grace & Co., 1979) and U.S. Pat. No. 4,271,043 (Grace & Co., 1981).

In a first aspect of the invention, there is provided a static ion-exchange process for the preparation of a polynuclear Al species, said process comprising the treatment of an aqueous aluminum chloride solution with a hydroxide-form ion-exchange resin at a temperature from 5° C. to 60° C. for a period of at least 30 minutes.

The invention enables the preparation of polynuclear Al species in very controlled conditions. The invention utilizes a "soft" hydrolysis-condensation process that is in marked contrast to the harsh conditions found in most processes involving reaction with hydroxide ions. This enables good control of the reaction and relatively easy running of the process. Most importantly, the invention enables the formation of particularly high levels of preferred polynuclear Al species, such as the $Al_{13}$-mer and, through further reaction, the $Al_{30}$-mer; moreover, this can be done at relatively high Al concentration.

The invention involves the use of reagents that are widely available and that have low cost: aluminum chloride and an anion exchange resin. The reagents are used efficiently and no excess of either reagent is required—this eliminates the need for post-reaction washing and/or other purification of the reaction product. In addition, the method does not require 'foreign' species (e.g. mercury) to be present, a fact that also reduces the need for post-reaction washing and/or other purification. The method is simple and produces a high purity product.

Many features of the process of the invention may give rise to environmental benefits, in particular low energy consumption and the use of reagents capable of being recycled (vide infra).

Polynuclear Al species are aluminum species comprising more than one aluminum nucleus. The invention is particularly useful in the preparation of the polynuclear Al species having more than two aluminum nuclei, especially those species known as the $Al_{13}$-mer and the $Al_{30}$-mer.

In preferred embodiments, the method of the invention is used in the preparation of an AP active, in particular a basic aluminum chloride AP active, and especially an ACH AP active, comprising polynuclear Al species. In especially preferred embodiments, the invention may be used to prepare AP actives having 90% or greater of the aluminum in the form of $Al_{13}$-mer and/or $Al_{30}$-mer.

The invention is typically used to prepare polynuclear Al species that do not contain any ligands other than hydroxide; however, polynuclear Al species prepared according to the invention may include species that are complexed with amino acids, such as glycine.

A key feature of the invention is the use of a hydroxide-form ion-exchange resin. Without wishing to be bound by theory, it is believed that the slow exchange of the hydroxide ion from the resin with chloride ions from solution helps to control the hydrolysis and condensation reactions leading to the production of the polynuclear Al species in high yield.

It is essential that the method of preparation involves a static ion-exchange process, as opposed to a dynamic ion-exchange process. A dynamic ion-exchange process is one in which there is physical flow of solution through a bed of ion-exchange resin, the bed typically being in the form of a column. Dynamic ion-exchange tends to lead to concentration perturbations, i.e. uneven concentrations of reactants at different physical locations within the ion-exchange bed. This is an unfavorable situation with regard to the achievement of the benefits of the present invention. In a static ion-exchange process according to the present invention, the aluminum chloride solution is mixed with the ion-exchange resin and the two are allowed to sit together. There is no bulk flow of the solution through a fixed bed of the resin. This process avoids the concentration perturbations inherent in dynamic ion-exchange. The resin:solute ratio is approximately equal at all physical locations when such a process is used. This is essential for the achievement of the benefits of the present invention.

The ion-exchange resin may be partially or fully in its hydroxide-form; however, the use of an ion-exchange resin that is initially fully in its hydroxide-form is preferred. As a precursory step, the hydroxide-form ion-exchange resin may be generated from an ion-exchange resin in an alternative form. Often ion exchange resins are bought in a chloride-form and the precursory step involves washing the resin with a hydroxide ion source, such as sodium or potassium hydroxide solution, in order to produce the hydroxide-form ion-exchange resin.

In order to maintain homogeneity, it is preferred that the mixture of ion-exchange resin and aluminum chloride solution is stirred during the reaction. The stirring is preferably done in a manner such that resin retains its integrity, i.e. in a manner such that the resin is not crushed in any way (crushed resin is harder to remove from the solution at the end of the reaction). Typically, an overhead stirrer made of a corrosion resistant shaft and blade is used. High-grade stainless steel is a suitable material for these components, chemically resistant glass is a preferred material for these components and Teflon is a particularly preferred material for these components. For economic and environmental reasons, it is desirable to operate at high concentrations. It is therefore preferred that the hydroxide-form ion-exchange resin has a high capacity, in particular a concentration of hydroxide ions of at least 1 $mol.kg^{-1}$ and especially a concentration of hydroxide ions of at least 2 $mol.kg^{-1}$. Such high capacities enable the resin to be kept mobile (i.e. stirred [vide supra]) at high concentrations ($mol.dm^{-3}$) of hydroxide ion in the total reaction mixture. For the same reasons, it is also preferred that the ion-exchange resin has a relatively small average bead size. It is preferred that the average bead size (wet) is 75 mesh or less and it is particularly preferred that the average bead size (wet) is 50 mesh or less.

Having a high concentration of hydroxide ion in the total reaction mixture also enables one to have a high concentration of aluminum chloride in the total reaction mixture, the ratio of one to the other being fixed within relatively narrow bounds, dependent upon the nature of the polynuclear Al species desired (vide infra). The concentration of aluminum chloride in the total reaction mixture is typically from 0.05 $mol.dm^{-3}$ to 0.6 $mol.dm^{-3}$ and is preferably from 0.1 $mol.dm^{-3}$ to 0.4 $mol.dm^{-3}$. For hydroxide-form ion-exchange resin having a particularly high capacity, for example at least 2 $mol.kg^{-1}$, the concentration of aluminum chloride in the total reaction mixture may be higher, for example at least 0.4 $mol.dm^{-3}$ and optionally up to 0.6 $mol.dm^{-3}$.

The ion-exchange resin used in the present invention is insoluble in water and in the continuous phase of the reaction mixture, i.e. aqueous aluminum chloride solution. Typically, the ion-exchange resin contains weakly basic, e.g. polyamine, matrix active groups.

Prior to mixing with the aluminum chloride solution, it is preferred that the hydroxide-form ion-exchange resin is suspended in water. This allows equilibration of the resin with the aqueous medium, such equilibration being beneficial to the quality of the eventual reaction product.

The ion-exchange resin may be added to the solution of aluminum chloride or vice versa. For optimum ease of operation and control of the reaction, it is preferred that the solution of aluminum chloride is added to an aqueous suspension of ion-exchange resin.

In a preferred embodiment of the invention, a strong acid (i.e. an acid having a $pK_a$ of less than 2.5), typically hydrochloric acid, is added to the reaction mixture during the mixing of the aluminum chloride solution with a suspension of the ion-exchange resin. Addition of the acid serves to reduce the pH shock that can occur during this mixing, thereby minimising the production of undesirable components. The acid may be added independently of, or as a component of, either the aluminum chloride solution or the suspension of ion-exchange resin or both.

In a particularly preferred embodiment, a strong acid is added to the suspension of ion-exchange resin shortly before this is mixed with the aluminum chloride solution. It is preferred that sufficient acid is added to give the suspension of ion-exchange resin approximately the same pH as the solution of aluminum chloride with which it is to be mixed. It is particularly preferred that the suspension of ion-exchange resin and the aluminum chloride solution have a pH within 1 unit of each other when they are mixed. In this embodiment, it is important that the mixing is performed quickly, preferably being completed within two minutes and more preferably within one minute of the completion of the acidification of the suspension of ion-exchange resin. It is important that this time is minimized in order to minimize premature neutralisation of the added acid by the hydroxide ions present within the ion-exchange resin. When the scale of the reaction is too great for these preferred mixing times to be achieved, it may be possible to acidify the suspension of ion-exchange resin in small portions or by drip-feed shortly before it is passed into the aluminum chloride solution.

An important parameter in the method of the invention is the ratio of hydroxide ion equivalents to aluminum ion equivalents in the reaction mixture, this ratio being termed the hydrolysis ratio:H. For generation of polynuclear Al species, in particular the $Al_{13}$-mer, H is preferably from 2.1 to 2.6, more preferably from 2.3 to 2.5, and most preferably from 2.4 to 2.5. For generation of $Al_{13}$-mer H is most preferably about 2.45, while for generation of the $Al_{30}$-mer, H is most preferably about 2.40. It is preferred that the source of the hydroxide ions is solely the hydroxide-form ion-exchange resin. It is preferred that the source of the aluminum ions is solely the aluminum chloride solution.

The pH of the reaction mixture increases during the course of the preparation, especially during the early stages. The initial pH is typically below 3.5 and, to optimise production of polynuclear Al species, it is preferred that the pH is kept below 4.75 throughout the course of the preparation.

The rate of increase of the reaction pH (i.e. d(pH)/dt) preferably decreases during the course of the reaction. It is particularly preferred that d(pH)/dt does not increase during any period of the preparation. It is especially preferred that d(pH)/dt has reduced to less than 0.015 within 30 minutes of the aluminum chloride solution and ion-exchange resin being mixed, pH being conventional units ($-\log_{10}[H^+]$), and time t being expressed in minutes.

The preparation is preferably carried out at a temperature of from 18° C. to 40° C., more preferably at from 20° C. to 35° C., and most preferably at from 20° C. to 30° C. Lower temperatures are not desirable because they tend to slow the reaction down. Higher temperatures are not desirable because they tend to lead to a lower quality product, having greater inhomogeneity and/or a lower level of polynuclear Al species.

The time during which the aluminum chloride solution and ion-exchange resin are in contact is preferably at least 45 minutes, more preferably at least 1 hour, and most preferably at least 2 hours. Shorter reaction times are undesirable because the reaction may not have reached the optimum extent of completion. For economic reasons and/or product quality reasons, it is preferred that the reaction time is not too great. The reaction time is preferably less than 6 hours, more preferably less than 4 hours, and most preferably less than 3 hours.

To a certain extent, the optimum reaction temperature and time are related, shorter reaction times being required at higher temperatures and vice versa. Thus, in some embodiments it may be preferred that the reaction is carried out at from 10° C. to 25° C. for 2 to 4 hours, whilst in other embodiments it may be preferred that the reaction is carried out at from 25° C. to 40° C. for 30 minutes to 2 hours.

Following the reaction between the aqueous aluminum chloride solution and the hydroxide-form ion-exchange resin, the resin is removed from the solution, typically by filtration. Following this step, a small amount of further hydroxide-form ion-exchange resin (typically from 0.1% to 0.5% of the weight of resin initially used) may be added in order to achieve especially high yield of the desired polynuclear Al species. This further reaction is preferably performed at ambient temperature for a period of from 1 day to 1 week. The amount of further ion-exchange resin to be added may be calculated from an analysis of a portion of the solution of polynuclear species produced during the initial reaction.

In a preferred embodiment of the invention, washing the ion-exchange resin with a source of hydroxide ion (such as aqueous sodium or potassium hydroxide solution) is used as a means of regenerating the hydroxide form of the resin after it has been used in accordance with the invention. In such embodiments, the aqueous aluminum chloride solution is treated with the hydroxide-form ion-exchange resin, the ion-exchange resin is then separated from the resulting solution of polynuclear Al species, regenerated by treatment with a source of hydroxide ions, and then re-used to prepare further polynuclear Al species. This recycling of the ion-exchange resin adds to the efficiency and environmental acceptability of the manufacturing process. In a preferred version of this embodiment, the ion-exchange resin is washed with hydrochloric acid, typically of concentration about 10% w/v, prior to being washed with a source of hydroxide ion. The acid wash serves to remove residual aluminum species from the resin and thereby improve the performance of the regenerated resin.

It may be noted that when an ion-exchange resin is washed with a source of hydroxide ion, whether it be prior to use or re-use, it is highly desirable to remove residual free hydroxide ions from the resin by further washing it with water prior to said use or re-use.

Preparation of the $Al_{30}$-mer polynuclear species requires ageing of the solution of polynuclear species prepared according to the first aspect of the invention, following removal of the ion-exchange resin. In order to maximize the yield of $Al_{30}$-mer, the solution of polynuclear species prepared according to the first aspect of the invention may be aged at from 60 to 95° C., preferably at from 70 to 90° C., and more preferably at from 80 to 85° C. The ageing is preferably performed for from 12 to 72 hours, more preferably from 24 to 64 hours, and most preferably from 24 and 36 hours. In general, the longer the ageing time, the more complete is the transformation of lower species into the $Al_{30}$-mer species.

A process of preparation analogous to that described in the first aspect of the invention may be used to prepare aluminum hydroxide sols of surprisingly narrow particle size distribution. Such materials may be advantageous in the ceramics field and in chromatographic applications. The analogous process comprises the treatment of an aqueous aluminum salt solution with a hydroxide-form ion-exchange resin at a temperature from 5° C. to 60° C. for a period of at least 30 minutes, H being chosen to be greater than 2.6, preferably greater than 2.7, and more preferably greater than 2.8. The aluminum salt employed is preferably chloride, but may be nitrate or some other water-soluble salt. Following removal of the ion-exchange resin by filtration, a colloidal dispersion or sol of aluminum hydroxide remains. In a further step, this sol may be aged, preferable at 60° C. or less and preferably for one month or less, in order to produce an aluminum hydroxide sol of selected particle size. In general, the longer the ageing period employed, the greater is the particle size of the aluminum hydroxide colloidal dispersions produced. Higher ageing temperature also leads to larger particle sizes. Nano-sized colloidal dispersions of selected particle size may be produced in this manner.

The solution of aluminum species remaining after removal of the ion-exchange resin may be dried to give a solid sample of polynuclear Al species in powder form. This may be done on an industrial scale by freeze-drying or spray-drying. Freeze-drying is generally considered to be a less harsh technique and may be preferred for this reason. Spray drying tends to result in a dried salt with a more consistent and desirable particle size distribution and may be preferred for this reason.

When spray drying is used, it is preferred that the dried powder be cooled as soon as possible after the drying step, for example by conveying it from the drying stage to the next stage (e.g. a storage stage) in a cooled, low humidity current of air.

When the solution of aluminum species is dried to give an AP active, the procedure is performed to give a water content of the resulting (dried) AP active of preferably no lower than about 2%, more preferably at least about 4%, even more preferably at least 6%, and most preferably at least 8% by weight of the active. It is not desirable to dry to particularly low water levels, because the drying regimes to which the active needs to be subjected to get to such water levels may be deleterious to the quality of the active resulting, in particular its content of desirable polynuclear species, such as the $Al_{13}$-mer. With regard to the maximum level of water, the drying procedure is performed to give a water content of the resulting (dried) AP active of preferably less than 12% and more preferably less than 10% by weight of the active. It is believed that reducing the water content of the active is desirable for its long-term stability.

Water content may conveniently be measured using a moisture balance, for example a Sartorius MA30 moisture balance, used on an "auto" programme with a set point of 100° C.

EXAMPLES

A commercially available anion exchange resin (Amberlite IRA67, 50 mesh (wet), ex Sigma) was washed using deionized distilled water and was transformed into the hydroxide-form using 2M potassium hydroxide solution prior to a second extensive washing with water and drying for 48 hours under ambient conditions.

The titre of the resin was established using an excess of 1M hydrochloric acid solution and back-titration with a standard volumetric solution potassium hydrogen carbonate.

Various amounts of the hydroxide-form ion-exchange resin were suspended in 80 ml aliquots of deionized water. To these suspensions were added 20 ml aliquots of 1M aluminum chloride solution and the mixtures were stirred at 25±0.2° C. in a Pyrex glass reactor for 3 hours. After this time, the resin was removed by filtration through a 70 micron HDPE Buchner filter funnel to leave an aqueous solution of aluminum species as the final product.

The amount of the hydroxide-form ion-exchange resin was varied to give particular hydrolysis ratios H, H being the ratio of hydroxide ion equivalents to aluminum ion equivalents in the reaction mixture. H values from 0.5 to 3.0 were investigated.

The pH of each of the reaction mixtures was monitored throughout the procedure. From these measurements, it was clear that the procedure is a particularly "soft" hydrolysis technique. Evidence for this was that (a) there was no temporary pH shift due to local perturbations, as typically created by alkali addition; (b) each stage of the reaction, in particular the formation of the $Al_{13}$-mer, was well separated from the others on the time scale; and (c) there was no premature hydroxide formation at H values below about 2.5, as indicated by smooth plateaus on the corresponding pH curves. These results were supported by quantitative $^{27}Al$ NMR measurements (vide infra).

The effect of H upon the level of aluminum species in the final product is shown in Table 1. From these figures, it may be seen that levels of H from 2.1 to 2.6 all produce high levels of $Al_{13}$-mer, with H values of from 2.4 to 2.5 being particularly preferred for this purpose. It is noteworthy that aluminum hydroxide becomes the dominant species present at higher H values.

TABLE 1

| | % Aluminium present as ... | | |
|---|---|---|---|
| H | Mono- and bi-nuclear species | $Al_{13}$-mer | $Al(OH)_3$ |
| 0.5 | 92 | 8 | 0 |
| 0.75 | 79.5 | 20.5 | 0 |
| 1 | 67.7 | 32.3 | 0 |
| 1.25 | 54.7 | 45.3 | 0 |

TABLE 1-continued

| | % Aluminium present as ... | | |
|---|---|---|---|
| H | Mono- and bi-nuclear species | $Al_{13}$-mer | $Al(OH)_3$ |
| 1.5 | 43.7 | 56.3 | 0 |
| 1.75 | 33 | 67 | 0 |
| 2.1 | 17.5 | 82.5 | 0 |
| 2.2 | 15 | 85 | 0 |
| 2.3 | 9.6 | 90.4 | 0 |
| 2.4 | 7.2 | 92.8 | 0 |
| 2.5 | 2.6 | 91.8 | 5.6 |
| 2.6 | 1.5 | 71.7 | 26.8 |
| 2.7 | 1.3 | 47.9 | 50.8 |
| 2.8 | 1.8 | 29.8 | 68.4 |
| 2.9 | 2 | 13.1 | 84.9 |
| 3 | 2.3 | 5.9 | 91.8 |

Quantitative $^{27}Al$ solution NMR was used to determine the amounts of mono- and bi-nuclear species present and the amount of $Al_{13}$-mer present. The amount of aluminum hydroxide was calculated as the difference between the sum of these amounts and the amount of aluminum in the starting solutions (0.2 M), as described in the work of Deschaume et al, *Adv. Eng. Materials*, 6(10), 2004, 836.

In an analogous example, a portion of 1M aluminum chloride solution containing 0.25 M hydrochloric acid was added rapidly to a stirred suspension of hydroxide-form ion-exchange resin in 0.1 M hydrochloric acid, the time between acidification of the ion-exchange resin and addition of the acidified aluminum chloride solution being kept to a minimum. The amounts of reagents were selected to give an H value of 2.45 and a final aluminum concentration of 0.4 M. After equilibration had been achieved (approximately 3 hours), the resin was removed by filtration and the solution of aluminum species was left to stand at ambient temperature for one week. After this time, the speciation of the sample was re-checked and further hydroxide-form ion-exchange resin was added to raise the percentage of $Al_{13}$-mer present to near to 100%.

In a further example, a portion of 1M aluminum chloride solution containing 0.25 M hydrochloric acid was added rapidly to a stirred suspension of ion-exchange resin in 0.1 M hydrochloric acid, the time between acidification of the ion-exchange resin and addition of the acidified aluminum chloride solution being kept to a minimum. The amounts of reagents were selected to give an H value of 2.40 and a final aluminum concentration of 0.4 M. After equilibration had been achieved (approximately 3 hours), the resin was removed by filtration and the solution of aluminum species was heated at 85° C. for 38 hours. Analysis of the resulting solution revealed that greater than 90% of the aluminum was present as the $Al_{30}$-mer.

In a comparative example, a portion of aluminum chloride solution was repeatedly passed through a column packed with hydroxide-form ion-exchange column resin, the concentrations of hydroxide and aluminum being chosen to give H values of 2.45, 2.7 and 3.0 and an aluminum concentration of 0.4 M. Analysis of the resulting solutions revealed that $Al_{13}$-mer was present in only minor amounts in each. In addition, it was found that substantial amounts of aluminum ions were left on the column. This example illustrates some of the problems associated with a dynamic ion-exchange process. It is hypothesized that a pH gradient forms in front of aluminum solution as it flows through the column, resulting in the first portion of the solution getting 'over-hydrolyzed' and forming large aluminum hydroxide which get entrapped in the column. This in turn causes a deficiency of hydroxide ions on the resin surface available for production of polynuclear aluminum species and a low concentration $Al_{13}$-mer in the final product is the result.

In a further experiment, a portion of 1 M aluminum chloride solution containing 0.25 M hydrochloric acid was added rapidly to a stirred suspension of ion-exchange resin in 0.1 M hydrochloric acid, the time between acidification of the ion-exchange resin and addition of the acidified aluminum chloride solution being kept to a minimum. The amounts of reagents were selected to give an H value of 3.0 and a final aluminum concentration of 0.4 M. After 3 hours, the ion-exchange resin was removed by filtration and analysis of the resulting sol revealed that greater than 90% of the aluminum was present as aluminum hydroxide. The particle size of the aluminum hydroxide sol was determined to be approximately 17 nm by dynamic light scattering [DLS]. This sol was then divided into two equal parts. One part was stored at room temperature for 48 hours and produced a near mono-disperse aluminum hydroxide sol of mean particle size 35 nm, as determined by DLS. The other part was stored at 60° C. for 48 hours and produced a near mono-disperse aluminum hydroxide sol of mean particle size 80 nm, as determined by DLS.

The invention claimed is:

1. A static ion-exchange process for the preparation of polynuclear Al species comprising $Al_{13}$-mer and/or $Al_{30}$-mer, said process comprising treating a reaction mixture comprising an aqueous aluminum chloride solution and a hydroxide-form ion-exchange resin at a temperature of from 5° C. to 60° C. for a period of at least 30 minutes, wherein the ratio of hydroxide ion equivalents to aluminium ions in the reaction mixture, H, is from 2.1 to 2.6.

2. A process according to claim 1, wherein the concentration of aluminum chloride in the total reaction mixture is 0.05 $mol.dm^{-3}$ or greater.

3. A process according to claim 1, wherein the hydroxide-form ion-exchange resin has a capacity of at least 1 $mol.kg^{-1}$.

4. A process according to claim 1, wherein the mixture of ion-exchange resin and aluminum chloride solution is stirred during the reaction.

5. A process according to claim 1, wherein the ion-exchange resin is suspended in water prior to being mixed with the aluminum chloride solution.

6. A process according to claim 5, wherein a strong acid is added to the reaction mixture during the mixing of the aluminum chloride solution with the suspension of ion-exchange resin.

7. A process according to claim 6, wherein the strong acid is added to the suspension of ion-exchange resin shortly before this is mixed with the aluminum chloride solution, the mixing being completed within two minutes of the acidification of the ion-exchange resin.

8. A process according to claim 1, wherein the pH of the reaction mixture is kept below 4.75 throughout the course of the preparation.

9. A process according to claim 1, wherein $d(pH)/dt$ does not increase during any period of the preparation.

10. A process according to claim 1, wherein the hydroxide-form ion-exchange resin is separated from the resulting solution of polynuclear Al species, regenerated by treatment with a source of hydroxide ions, and then re-used to prepare further polynuclear Al species.

11. A process according to claim 1, wherein the resulting solution of polynuclear Al species is aged, following removal of the ion-exchange resin, in order to maximize the yield of $Al_{30}$-mer.

12. A process according to claim 11, wherein the resulting solution of polynuclear Al species is aged at from 60 to 95° C. for from 12 to 72 hours.

13. A process according to claim 1, wherein the resulting solution of polynuclear Al species is dried to give a solid sample of polynuclear Al species in powder form.

14. A process according to claim 1 wherein the reaction mixture is treated at a temperature of from 18° C. to 45° C. for a period of at least 45 minutes.

* * * * *